US006759394B2

(12) United States Patent  (10) Patent No.: US 6,759,394 B2
DeBenedetti et al.  (45) Date of Patent: Jul. 6, 2004

(54) CANCER GENE THERAPY BASED ON TRANSLATIONAL CONTROL OF A SUICIDE GENE

(75) Inventors: Arrigo DeBenedetti, Shreveport, LA (US); Robert J. DeFatta, Shreveport, LA (US)

(73) Assignee: Board of Supervisors of La. State Un. & Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 09/916,017

(22) Filed: Jul. 26, 2001

(65) Prior Publication Data

US 2003/0087852 A1 May 8, 2003

(51) Int. Cl.$^7$ .............................................. A61K 48/00

(52) U.S. Cl. ..................... 514/44; 435/320.1; 536/23.1; 536/24.1

(58) Field of Search ........................ 514/44; 435/320.1; 536/23.1, 24.1

(56) References Cited

U.S. PATENT DOCUMENTS

| | | | |
|---|---|---|---|
| 4,562,155 A | 12/1985 | Ricciardi et al. | |
| 5,646,009 A | 7/1997 | Rhoads et al. | |
| 6,020,162 A | 2/2000 | Burley et al. | |

FOREIGN PATENT DOCUMENTS

| | | |
|---|---|---|
| WO | WO0078803 | 12/2000 |
| WO | WO0140490 | 6/2001 |

OTHER PUBLICATIONS

Gibco–Brl catalogue, 1993–1994. p. 9–19 only.*
Tshimogori et al , Biochemical and Biophysical Research Communications, "Spermidine Regulation of Protein Synthesis at the Level of tiation Complex Formation of Mei–tRNA, mRNA and Ribosomes," 1996, 223, pp. 544–548.*
Benchmarks, BioTechniques, "Dominant Positive and Negative Selection Using Luciferase, Green Fluorescent Protein and beta–Gatactosides Reporter Gene Fusions." 2000, vol. 28, No. 2, pp. 210–214.*
P Workman et al., Trends in Molecular Medicine. "Translating basic cancer research into new cancer therapeutics," 2002, vol. 8. No. 4, pp. S1–S9.*
C Beck et al., The Thymidine Kinase/Ganciclovir–Mediated "Suicide" Effect Is Variable in Different Tumor Cells, pp. 1526–1528 and 1530, Human Gene Therapy, 1995.*
D Kirn et al., Trends in Molecular Medicine, "The emerging fields of suicide gene therapy and virotherapy," 2002, vol. 8, No. 4, pp. S68–S73.*
RG Crystal, Science, "Transfer of genes to Humans:Early Lessons and Obstacles to Success," Oct. 1995, vol. 270, pp. 404–410.*

IM Verma et al., Nature, "Gene therapy–promises, problems and prospects," Sep. 1997, vol. 389, pp. 239–242.*
W Walther et al., Drugs, "Viral Vectors for Gene Transfer, " Aug. 2000, 60, (2), 249–271.*
Anderson, L.M. et al., "Adenovirus–mediated tissue–targeted expression of the HSVtk gene for the treatment of breast cancer," Gene Therapy, vol. 6, pp. 854–864 (1999).
Anthony, B. et al., "Overexpression of the protooncogene–translation factor eIF–4E in breast carcinoma cell lines," Int.J.Cancer, vol. 65, pp. 858–863 (1995).
Binley, K. et al., "An adenoviral vector regulated by hypoxia for the treatment of ischaemic disease and cancer," Gene Therapy, vol. 6, pp. 1721–1727 (1999).
Clemens, M.J. et al., "Translational control: the cancer connection," Int. J. Biochem. Cell Biol., vol. 31, pp. 1–23 (1999).
Crew, J.P. et al., Eukaryotic initiation factor–4E in superficial and muscle invasive bladder cancer and its correlation with vascular endothelial growth expression and tumour progression, Br. J. Cancer, vol. 82, pp. 161–166 (2000).
De Benedetti, A. et al., "eIFA4 expression in tumors: its possible role in progression of malignancies," Int. J. of Biochemistry and Cell Biology, vol. 31, pp. 59–72 (1999).
DeFatta, R.J. et al., "A Cancer Gene Therapy Approach Through Translational Control of a Suicide Gene," submitted to Nature Medicine, Jul. 9, 2001.

(List continued on next page.)

*Primary Examiner*—Dave T. Nguyen
*Assistant Examiner*—J. Eric Angell
(74) *Attorney, Agent, or Firm*—Frost Brown Todd LLC

(57) ABSTRACT

A novel gene therapy for cancer has been discovered, which unlike most prior appraches, does not require specific knowledge of the cancer cells, but instead targets a general characteristic that distinguishes cancer cells from normal cells, i.e., elevated eIF4E expression. The expression of a toxin or conditional toxin such as HTK is translationally repressed in normal cells by placing a complex 5' UTR in front of its reading frame. In prototype experiments, this HTK mRNA, a transcriptional product of the BK-UTK vector, was translationally regulated so as to largely inhibit its production in normal murine and human cells, while cancer cells efficiently translated the protein, which a resulting increased sensitivity to GCV. Synthesis of the HTK protein from the BK-UTK vector (containing the 5' UTR of Fibroblast growth factor –2 ("FGF-2") readily occurred in a panel of murine and human breast carcinoma lines, but not in normal cell lines. Subcutaneous tumors and experimental lung metastases of the breast carcinoma line MM2MT in BALB/c mice were greatly reduced by transfection with the BK-UTK vector, followed by GCV administration. Both the BK-UTK and the BK-TK (control) vectors were effective in reducing lung metastasis following systemic delivery of the vectors and subsequent GCV administration. However, the BK-TK vector was highly toxic to mice while little to no toxicity was seen in mice treated with the BK-UTK vector.

17 Claims, 6 Drawing Sheets

OTHER PUBLICATIONS

DeFatta, Robert J., "The Eukaryotic Translational Initiation Factor (eIF) 4E During Cancer Progression and as a Target for Cancer Gene Therapy," a Dissertation, submitted to the Graduate Faculty of Medical Center of Louisiana State University and Agricultural and Mechanical College, catalogued and placed on the shelf on Mar. 20, 2001.

DeFatta, R.J. et al., "Selective Killing of Cancer Cells Based on Transitional Control of a Suicide Gene," submitted to Nature Medicine, Jul. 9, 2001.

Goldfarb, R.H. et al., "Therapeutic agents for treatment of established metastases and inhibitors of metastatic spread: preclinical and clinical progress," Current Opinion in Oncology, vol. 4, pp. 1130–1141 (1992).

Gomez–Navarro, J. et al., "Gene therapy for cancer," European Journal of Cancer, vol. 35(6), pp. 2039–2057 (1999).

Hall, S.J. et al., "Cooperative therapeutic effects of androgen ablation and adenovirus–mediated herpes simplex virus thymidine kinase gene and ganciclovir therapy in experimental prostate cancer," Cancer Gene Therapy, vol. 6, pp. 54–63 (1999).

Herman, J.R. et al.,"In situ gene therapy for adenocarcinoma of the prostate: A phase I clinical trial," Human Gene Therapy, vol. 10, pp. 1239–1249 (1999).

Kaloss, M. et al., "Distribution of retroviral vectors and vector producer cells using two routes of administation in rats," Gene Therapy, vol. 6, pp. 1389–1396 (1999).

Kerekatte, V.V. et al., "The proto–oncogene/translation initiation factor eIF4E: a survey of its expression in breast carcinomas," Int. J. Cancer., vol. 64, pp. 27–31 (1995).

Kevil, C. et al., "Translational enhancement of FGF–2 by eIF–4 factors, and alternate utilization of CUG and AUG codons for translation initiation," Oncogene, vol. 11, pp. 2339–2348 (1995).

Kevil, C. et al., "Translational regulation of Vascular Permeability Factor by eukaryotic initiation factor 4E: Implications for tumor angiogenesis," Int. J. Cancer, vol. 65, pp. 785–790 (1996).

Klatzmann, D. et al., "A Phase I/II dose–escalation study of herpes simplex virus type 1 thymidine kinase "suicide" gene therapy for recurrent metastatic melanoma," Human Gene Therapy, vol. 9, pp. 2585–2894 (1998).

Koromilas, A.E. et al., "mRNAs containing extensive secondary structure in their 5' non–coding region translate efficiently in cells overexpressing initiation factor eIF–4E," The EMBO Journal, vol. 11, pp. 4153–4158 (1992).

Long, Z. et al., Molecular evaluation of biopsy and autopsy specimens from patients receiving in vivo retroviral gene therapy, Human Gene Therapy, vol. 10, pp.: 733–740 (1999).

Miyagi, Y. et al., "Elevated levels of eukaryotic initiation factor eIF–4E mRNA in a broad spectrum of transformed cell lines," Cancer Letters, vol. 91, pp. 247–252 (1995).

Nathan, C.O. et al., "Detection of the proto–oncogene eIF4E in surgical margins may predict recurrence in head and neck cancer," Oncogene, vol. 15, pp. 579–584 (1997).

Ramesh, R. et al., "In vivo analysis of the 'bystander effect': a cytokine cascade," Experimental Hematology, vol. 24, pp. 829–838 (1996).

Rosenwald, I.B., "Upregulatation expression of the genes encoding translation initiation factors eIF–4E and eIF–2alpha in transformed cells," Cancer Letters, vol. 102, pp. 113–123 (1996).

Rosenwald, I.B. et al., "Upregulated of protein synthesis initiation factor eIF4E is an early event during colon carcinogenesis," Oncogene, vol. 18, pp. 2507–2517 (1999).

Roth, J.A. et al., "Gene therapy for cancer: what have we done and where are we going?" Journal of the National Cancer Institute, vol. 89(1), pp. 21–39 (1997).

Scott, P.A.E. et al., "Differential expression of vascular endothetial growth factor mRNA versus protein isoforms expression in human breast cancer and relationship to eIF4E," British. J. Cancer, vol. 77, pp. 2120–2128 (1998).

Dove, Alan; "Gene Therapy—Work in Progress", Nature Medicine, vol. 8, No. 7, Jul. 2002.

Eck, Stephen L., "The Prospect for Gene Therapy," http://www.hosppract.com/genetics/9910mmc/htm, Apr. 12, 2002.

DeFatta, R.J., et al, "Selective killing of cancer cells through translational regulation of the HTK/GCV gene therapy system," http://www.cancerprev.org/Meetings/2002/Abstracts/1191/533, 2002.

Nathan, Cherie–Ann, "Technology and/or Marker Testing in a Clinical Setting Research Projects—Molecular Analysis of Surgical Margins with EIF4E in Can," http://researchportfolio.cancer.gov/cgi–bin/abstract.pl?Term=21&CSO=4.3&ProjectID=20; (Apr. 12, 2002).

Nathan, Cherie–Ann, et al., "COX–2 Expression in Dysplasia of the Head and Neck," Cancer, vol. 92, No. 7, Oct. 1, 2001.

Steiner, et al., "Gene therapy for prostate cancer," Gene Therapy and Molecular Biology, vol. 4, pp. 233–2 Dec., 1999.

Shariat, S.F., et al., "Adenovirus–mediated transfer of inducible caspases: a novel 'death switch' therapeutic approach to prostate cancer," http://www.ncbi.nlm.nih.gov/entrez/query.fcgi?cmd=Retrieve&db–PubMed&list.pids–11; (Apr. 12, 2002).

Ring, C.J., et al., Suicide gene expression induced in tumour cells transduced with recombinant adenov retroviral and plasmid vectors containing the ERBB2 promo http://www.ncbi.nlm.nih.gov/entrez/query.fcgi?cmd=Retrieve&db–PubMed&list.pids–89; (Apr. 12, 2002).

Martinez–Salas, Encarnacion, Internal ribosome entry site biology and its use in expression vect Biotechnology, 10:458–464; 1999.

Taylor, Diane, "Inhibition of eIF4E using mimetic peptides in cells induces apoptosis without affecting transcription," Research and Innovation Services. 2000.

Quicho, Florante A., et al, "Structural basis of mRNA cap recognition by proteins," Structural Biology, 10:78–86;2000.

Burley, Stephen K., "Eukaryotic Gene Regulation and Molecular Recognition," Zhoward Hughes Medical Institute, http://www.hhmi.org/research/investigators/burley.html; (Mar. 19, 2002).

Guba, Markus, et al, "Rapamycin inhibits primary and metastatic tumor growth by antiangiogensis: involvement of vascular endothelial growth factor," Nature Medicine, vol. 8, No. 2, Feb., 2002.

Raught, Brian, et al, "The target of rapamycin (TOR) proteins," PNAS, vol. 98, No. 13, 7037–7044; Jun. 19, 2001.

Polunovsky, Vitaly A., et al., :A Novel Approach to Increase Breast Cancer Chemosensitivity: Disruption of the Anti–Apoptotic Function of Translation Factor eIF4E Order, http://65.105.56.185/mater3/category21/A162983.html; (Mar. 19, 2002).

Seif, Isabelle, et al., "The Genome of Human Papovavirus BKV," Cell, vol. 18, 963–977, Dec. 1979.

De Benedetti, Arrigo, et al., "Novel BK virus–based episomal vector for expression of foreign genes in mammalian cells," Nucleic Acids Research, vol. 19, No. 8, 1924–1931; (1991).

Johannes, Gregg, et al., "Identification of eukaryotic mRNAs that are translated at reduced cap binding complex eIF4F concentrations using a cDNA microarray," PNAS, vol. 96, No. 23, 13118–13123; Nov. 9, 1999.

Van der Velden, Alike W., et al, "The role of the 5'untranslated region of an mRNA in translation regulation during development," Biochemistry & Cell Biology, 31, 87–106 (1999).

Barve, Shirish S., "Mechanism of Differential Regulation of IL–2 in Murine Th1 and Th2 T Cell Subsets," Journal of Immunology, 1172–1181 (1994).

Hentze, Matthias W., "Translational regulation: versatile mechanisms for metabolic and developmental control," Cell Biology, 7:393–398; (1995).

McKendrick, Linda, et al, "Translation initiation factor 4E," Biochemistry & Cell Biology, 31:31–55; (1999).

Pestova, Tatyana V., "Molecular mechanisms of translation initiation in eukaryotes," PNAS, vol. 98, No. 13, 7029–7036, Jun. 19, 2001.

Rau, Michael, et al, "A Reevaluation of the Cap–binding Protein, eIF4E, as a Rate–limiting Factor for Initiatic of Translation in Reticulocyte Lysate," Journal of Biological Chemistry, vol. 271, No. 15, 8983–8990; Apr. 1, 1996.

De Benedetti, Arrigo, et al, "Overexpression of eukaryotic protein synthesis initiation factor 4E in HeLa cel results in abberrant growth and morphology," Proc. Natl. Acad. Sci. USA, vol. 87, pp. 8212–8216, Nov. 1990.

Rinker–Schaeffer, Carrie W., "Decreasing the Level of Translation Initiation Factor 4E with Antisense RN Causes Reversal of ras–Mediated Transformation and Tumorigenesis of Cloned Rat Embryo Fibroblasts," Int. Cancer; 55, 841–847 (1993).

Graff, Jeremy R., "Reduction of Translation Initiation FAC Decreases the Malignancy of ras–Transfo Cloned Rat Embryo Fibroblasts," Int. J. Cancer; 60, 255–263 (1963).

Graff, Jeremy R., "Translation of ODC mRNA and Polyamine Transport are Suppressed in ras–Transformed CREF Cells by Depleting Translation Initiation Factor 4E," Biochemical and Biophysical Research Communications, 240, 15–20 (1997).

Sonenberg, Nahum, "Translation factors as effectors of cell growth and tumorigenesis," Cell Biology 5:955–960 (1993).

Lazaris–Karatzas, Anthoula, et al, "Malignant transformation by a eukaryotic initiation factor subunit that binds to mRNA 5' cap," Nature, vol. 345, Jun. 7, 1990.

Sonenberg, Nahum, et al., "The mRNA 5' cap–binding protein eIF4E and control of cell growth," Cell Biology, 10:286–275 (1998).

Raught, Brian, et al., "eIF4E activity is regulated at multiple levels," Journal of Biochemistry and Cell Biology, 31:43–57 (1999).

Rosenwald, Igor B., "Deregulation of protein synthesis as a mechanism of neoplastic transformation," BioEssays, vol. 18, No. 3, 243–250 (1996).

Rosenwald, Igor B., "Growth factor–independent expression of the gene encoding eukaryotic translation initiation factor 4E in transformed cell lines," Cancer Letters, 98:77–82 (1995).

Rosenwald, Igor B., "Upregulated expression of the genes encoding translation initiation factors 3IF–4E and eIF–2a in transformed cells," Cancer Letters, 102:113–123; (1996).

Willis, Anne E., "Translational control of growth factor and proto–oncogene expression," Biochemistry & Cell Biology, 31:73–86 (1999).

Zimmer, Stephen G., et al., "Translation Control of Malignancy: the mRNA cap–Binding Protein, eIF–4E, as a Central Regulator of Tumor Formation, Gorwth, Invasion and Metastasis," Anticancer Research, 20:1343–1352 (2000).

Nathan, Cherie –Ann O., et al., "Expression of eIF4E During Head and Neck Tumorigenesis: Possible Role in Angiogenesis," Laryngoscope, 109:1253–1258; Aug., 1999.

Li, Benjamin D. L., et al, Overexpression of Eukaryotic Initiation Factor 4E (eIF4E) in Breast Carcino Cancer, vol. 79, No. 12, Jun. 15, 1997.

Keene, Jack D., "Ribonucleoprotein infrastructure regulating the flow if genetic information between genome and the proteome," PNAS, vol. 98, No. 13, 7018–7024; Jun. 19, 2001.

Schmidt, Emmett V., "The role of c–myc in cellular growth control," Oncogene, 18:2988–2996 (1996).

Keiper, Brett D., et al., "Protein synthesis initiation factor 4G," Biochemistry & Cell Biology, 31:37–41; (1999).

Hoick, Martin, et al., "Internal ribosome initiation of translation and the control of cell death," TIG, vol. 16, No. 10, Oct., 2000.

Kimball, Scot R., "Eukaryotic initiation factor eIF2," Biochemistry & Cell Biology, 31:25–29 (1999).

McCormick, F., "Cancer gene therapy: fringe or cutting edge?" Nature Rev. Cancer, 1(2):130–41 (2001).

Miller, A.D., "Human gene therapy comes of age," Nature, 357:455–460 (1992).

* cited by examiner

1. BK-TK
2. BK-UTK

CANCER GENE THERAPY BASED ON TRANSLATIONAL CONTROL OF A SUICIDE GENE

The development of this invention was partially funded by the Government under grant CA69148 awarded by the National Institute of Health. The Government has certain rights in this invention.

This invention pertains to a translational control element placed in a vector to cause a selective translation of a toxin, including a toxin that acts by metabolizing a drug to become toxic (a "conditional toxin," e.g., the herpes simplex virus type-1 thymidine kinase (HTK)/ganciclovir interaction), inside solid tumor cells, while leaving normal cells unaffected due to their inability to translate the toxin encoded by the vector.

The major determinant of morbidity and mortality for patients with a primary malignant tumor is the emergence and progression of metastatic islets resistant to conventional therapy. It has been estimated that at least 50% of patients presenting with a primary tumor already bear metastases at the time of diagnosis. See R. H. Goldfarb et al., "Therapeutic agents for treatment of established metastases and inhibitors of metastatic spread: preclinical and clinical progress," Current Opinion in Oncology, vol. 4, pp. 1130–41(1992). Cancer gene therapy has developed as a means of attacking cancers resistant to conventional approaches. Much of the work has been directed at targeting characteristics of the primary tumor, with attention to choice of vector and transcriptional regulation. Two examples of this are the use of tissue-specific promoters and inducible promoters. See K. Binley et al., "An adenoviral vector regulated by hypoxia for the treatment of ischaemic disease and cancer," Gene Therapy, vol. 6, pp. 1721–1727 (1999). Despite some advances, these approaches have not successfully addressed the major problem of how to target metastases. Not only are metastases more difficult to reach but, due to their heterogeneity, they frequently do not maintain the specific gene expression pattern of the primary tumor, upon which gene therapy is generally designed. See S. J. Hall et al., "Cooperative therapeutic effects of androgen ablation and adenovirus-mediated herpes simplex virus thymidine kinase gene and ganciclovir therapy in experimental prostate cancer," Cancer Gene Therapy, vol. 6, pp. 54–63 (1999). There is an unfilled need for an effective in vivo cancer gene therapy that permits selective killing of both the primary tumor and distant metastases, while distinguishing cancer cells from normal cells.

One of the main obstacles to gene therapy has been the difficulty of successfully targeting cancer cells, while not harming normal cells. Indeed, it has been found that even when therapeutic vectors are delivered locally to a primary tumor, systemic effects still often occur, indicating that the vector has become blood-borne. See Z. Long et al., "Molecular evaluation of biopsy and autopsy specimens from patients receiving in vivo retroviral gene therapy, Human Gene Therapy, vol. 10, pp.:733–40 (1999); and M. Kaloss et al., "Distribution of retroviral vectors and vector producer cells using two routes of administration in rats," Gene Therapy, vol. 6, pp. 1389–1396 (1999). One approach to circumvent this problem is to use elements allowing specific transcriptional regulation of the vector, e.g., the use of tissue-specific promoters and inducible promoters. See Binley et al., 1999; and L. M. Anderson et al., "Adenovirus-mediated tissue-targeted expression of the HSVtk gene for the treatment of breast cancer," Gene Therapy, vol. 6, pp. 854–864 (1999). While these approaches are very promising, they require specific knowledge of the cancer cells, and are not applicable to most situations.

The use of suicide genes is one of the most promising strategies for gene therapy of solid tumors. Transfection of the herpes simplex virus type-1 thymidine kinase gene (HTK), given in combination with the drug ganciclovir (GCV), is the most commonly used cancer gene therapy system to date, both in experimental models and clinical trials. See J. Gomez-Navarro et al., "Gene therapy for cancer," European Journal of Cancer, vol. 35, pp. 867–885 (1999). HTK, whose substrate specificity is distinct from that of cellular thymidine kinases, can convert GCV to the toxic phosphorylated form, specifically killing the cells that express HTK. Since the concept of an HTK/GCV system was first described, it has shown good success as a tumor ablation strategy in a variety of experimental models. In addition, over two dozen clinical gene therapy trials based on this model have been initiated in the last seven years. See J. A. Roth et al., "Gene therapy for cancer: what have we done and where are we going?" Journal of the National Cancer Institute, vol. 89(1), pp. 21–39 (1997); D. Klatzmann et al., "A Phase I/II dose-escalation study of herpes simplex virus type 1 thymidine kinase "suicide" gene therapy for recurrent metastatic melanoma," Human Gene Therapy, vol. 9, pp. 2585–2894 (1998); and J. R. Herman et al.,"In situ gene therapy for adenocarcinoma of the prostate: A phase I clinical trial," Human Gene Therapy, vol. 10, pp. 1239–1249 (1999).

The HTK/GCV system is appealing due to its low inherent toxicity. Moreover, it has been shown that when as few as 10% of the cancer cells express HTK, it is still possible to obtain complete tumor ablation due to the "bystander effect" and specific immune responses. See R. Ramesh et al., "In vivo analysis of the 'bystander effect': a cytokine cascade," Experimental Hematology, vol. 24, pp. 829–838 (1996).

To direct the expression HTK primarily in cancer cells, most research to date has been based on either specific transcriptional regulation or specific delivery methods. Two examples of the former strategy are the use of tissue-specific promoters and inducible promoters. See Anderson et al., 1999; and Binley et al., 1999.

The protein eIF4E is the cap-binding subunit of the eIF4F complex, an ATP-dependent helicase that unwinds "excess" secondary structure in the 5' untranslated region (UTR) of mRNAs. The low-abundance of eIF4E/F is the limiting factor for the translation of some mRNAs, particularly those with long, G/C-rich 5' UTRs with the potential to form a stable, secondary structure. See M. J. Clemens et al., "Translational control: the cancer connection," Int. J. Biochem. Cell Biol., vol. 31, pp. 1–23 (1999). Overexpression of eIF4E results in a specific increase in the translation of these weakly competitive mRNAs, many of which encode products that stimulate cell growth and angiogenesis, like FGF-2 and VEGF. See C. Kevil et al., "Translational enhancement of FGF-2 by eIF-4 factors, and alternate utilization of CUG and AUG codons for translation initiation," Oncogene, vol. 11, pp. 2339–2348 (1995); C. Kevil et al., "Translational regulation of Vascular Permeability Factor by eukaryotic initiation factor 4E: Implications for tumor angiogenesis," Int. J. Cancer, vol. 65, pp. 785–790 (1996); and P. A. E. Scott et al., "Differential expression of vascular endothelial growth factor mRNA versus protein isoforms expression in human breast cancer and relationship to eIF4E," British. J. Cancer, vol. 77, pp. 2120–2128 (1998).

Elevating eIF4E rescues the translation of repressed mRNAs with a complex 5' UTR, many of which encode factors required for cell proliferation, e.g., protooncogene c-myc, cyclin D1, ornithine decarboxylase, fibroblast growth factor-2 (FGF-2), and vascular endothelial growth factor ("VEGF," otherwise known as vascular permeability factor, "VPF"). See A. De Benedetti et al., "eIF4E expression in tumors: its possible role in progression of malignancies," Int. J. of Biochemistry and Cell Biology, vol. 31, pp. 59–72 (1999).

Overexpression of eIF4E has been shown to be ubiquitous in solid tumors, including bladder, breast, cervical, colon, head and neck, and prostate, as well as in many malignant cell lines. See J. P. Crew et al., Eukaryotic initiation factor-4E in superficial and muscle invasive bladder cancer and its correlation with vascular endothelial growth factor expression and tumour progression," Br. J. Cancer, vol. 82, pp. 161–166 (2000); V. V. Kerekatte et al., "The protooncogene/translation initiation factor eIF4E: a survey of its expression in breast carcinomas," Int. J. Cancer., vol. 64, pp. 27–31 (1995); I. B. Rosenwald et al., "Upregulation of protein synthesis initiation factor eIF4E is an early event during colon carcinogenesis," Oncogene, vol. 18, pp. 2507–2517 (1999); C. O. Nathan et al., "Detection of the proto-oncogene eIF4E in surgical margins may predict recurrence in head and neck cancer," Oncogene, vol. 15, pp. 579–584 (1997); Y. Miyagi et al., "Elevated levels of eukaryotic initiation factor eIF-4E mRNA in a broad spectrum of transformed cell lines," Cancer Letters, vol. 91, pp. 247–252 (1995); B. Anthony et al., "Overexpression of the protooncogene- translation factor eIF-4E in breast carcinoma cell lines," Int. J. Cancer, vol.65, pp. 858–863 (1996); and I. B. Rosenwald, "Upregulated expression of the genes encoding translation initiation factors eIF-4E and eIF-2alpha in transformed cells," Cancer Letters, vol. 102, pp. 113–23 (1996).

We have discovered a novel gene therapy for cancer, which unlike most prior appraches, does not require specific knowledge of the cancer cells, but instead targets a general characteristic that distinguishes cancer cells from normal cells, i.e., elevated eIF4E expression. The expression of a toxin or conditional toxin such as HTK is translationally repressed in normal cells by placing a complex 5' UTR in front of its reading frame. In prototype experiments, this HTK mRNA, a transcriptional product of the BK-UTK vector, was translationally regulated so as to largely inhibit its production in normal murine and human cells, while cancer cells efficiently translated the protein, which a resulting increased sensitivity to GCV. Synthesis of the HTK protein from the BK-UTK vector (containing the 5' UTR of fibroblast growth factor –2 ("FGF-2")) readily occurred in a panel of murine and human breast carcinoma lines, but not in normal cell lines. Subcutaneous tumors and experimental lung metastases of the breast carcinoma line MM2MT in BALB/c mice were greatly reduced by transfection with the BK-UTK vector, followed by GCV administration. Both the BK-UTK and the BK-TK (control) vectors were effective in reducing lung metastasis following systemic delivery of the vectors and subsequent GCV administration. However, the BK-TK vector was highly toxic to mice while little to no toxicity was seen in mice treated with the BK-UTK vector.

Unlike prior gene therapy approaches that require specific knowledge of particular cancer cells, the novel strategy targets a general characteristic that distinguishes cancer cells from normal cells, i.e., elevated eIF4E expression. This property was exploited to repress the expression of a toxin translationally by placing a complex 5' UTR in front of its open reading frame. Without being bound by this theory, it is believed that cancer cells, which have higher levels of eIF4E and hence increased helicase activity, are able to continue to translate this hybrid HTK mRNA (UTK) while normal cells are not. In one embodiment, we used the 5' UTR of basic fibroblast growth factor (FGF-2), an angiogenic factor previously found to be translationally regulated by eIF4E. See Kevil et al., 1995. However, other complex hairpin sequences could be used for translational enhancement by eIF4E, e.g., sequences on genes of the proto-oncogene c-myc, cyclinD1, ornithine decarboxylase, or vascular endothelial growth factor ("VEGF"). See DeBenedetti et al., 1999. It is preferred that a DNA sequence comprise a natural or synthetic hairpin conformation with a stability of at least about $\Delta G \geq 50$ Kcal/mol. To achieve this stability and thus a tight hairpin formation, a relatively long palindromic oligonucleotide sequence that is self-complementary is required. See A. E. Koromilas et al., "mRNAs containing extensive secondary structure in their 5' non-coding region translate efficiently in cells overexpressing initiation factor eIF-4E," The EMBO Journal, vol. 11, pp. 4153–4158 (1992); and A. DeBenedetti et al., 1999.

The cancer cell lines were shown to translate the UTK mRNA and thus synthesize HTK protein, while normal cell lines did not. Accordingly, only cancer cells were killed by low concentrations of ganciclovir. By altering the expression of eIF4E it was possible to alter the sensitivity of normal and cancer cell lines to ganciclovir.

Expression of eIF4E is elevated in most solid tumors, causing translation of mRNAs that would normally be repressed by complex 5' UTRs. A translational control element was incorporated into a vector (BK-UTK) that we designed to express HTK. This and a control vector (BK-TK) were used to treat experimental tumors of a murine breast cancer line. Both vectors were equally effective in reducing subcutaneous tumors and lung metastases with gancyclovir administration. However, the BK-TK vector was highly toxic, resulting in severe weight loss, degeneration of various organs, and early death of mice following systemic vector delivery. In contrast, the BK-UTK increased median survival.

The following table lists and defines the common abbreviations used in the specification and claims.

Figure 1A:
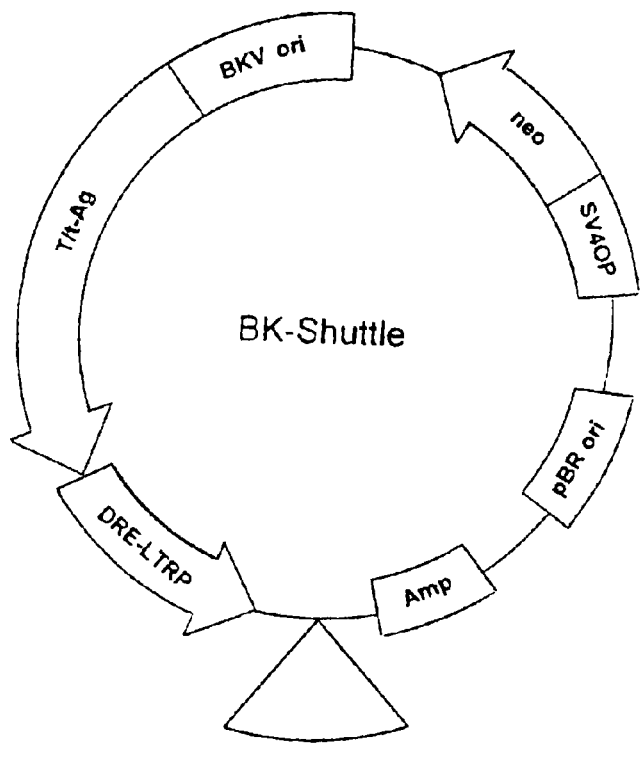
FIG. 1a schematically illustrates the BK-Shuttle vector and the insertion point of both the HTK cDNA and the hybrid FGF-2/HTK cDNA to produce the BK-TK and the BK-UTK vectors.
Figure 1B:
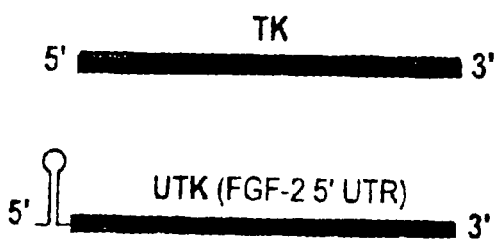
FIG. 1b schematically illustrates the HTK cDNA and the hybrid FGF-2/HTK cDNA.

FIG. 1a and described in I. Sief et al., Cell, vol. 18: 963–977 (1979)), as described in A. De Benedetti et al., "A novel BK virus-based episomal vector for expression of foreign genes in mammalian cells," Nucleic Acids Research, vol. 19, pp. 1925–1931 (1991). This construct is referred to as "BK-TK." In the BK-UTK vector, the HTK sequence was preceded by 650 bases of the 5'UTR of the rat FGF-2 (as described in R. Z. Florkievicz et al., Growth Factors, vol. 4, pp. 265–275(1991)). The BK-Shuttle vector as shown in FIG. 1a was chosen to drive the expression of the HTK gene because it allows high-copy episomal expression. FIG. 1b illustrates the normal HTK cDNA (BK-TK) and the hybrid HTK (BK-UTK) constructs. Note the addition of the 650 bp 5' UTR from the rat FGF-2 5'UTR shown as a hairpin with a predicted stability of −55 Kcal/mol, which is highly inhibitory to cap-dependent translation. See C. Kevil, et al, "Translational enhancement of FGF-2 by eIF-4 factors, and alternate utilization of CUG and AUG codons for translation initiation," Oncogene, vol. 11, pp. 2339–2348 (1995).

Each vector was then stably transfected into either MM3MG cells (ATCC No.CRL6376, a normal mouse mammary line) or MM2MT cells (ATCC No. CRL6373, a mouse

TABLE 1

Abbreviations

A. Proteins

| | | |
|---|---|---|
| | FGF-2 | Fibroblast growth factor-2 |
| | GCV | Ganciclovir |
| | HTK | Herpes simplex virus type-1 thymidine kinase |

B. RNA or DNA

| | | |
|---|---|---|
| | UTR | 5' Untranslated region of mRNA |
| | eIF4E | Cap-binding sub-unit of the eIF4F complex |
| | 4E-AS | eIF4E Antisense RNA |

C. Cell Lines

| | | |
|---|---|---|
| | MM3MG | Normal mouse mammary line; ATCC No. CRL6376 |
| | MM2MT | Mouse mammary carcinoma cell line; ATCC No. CRL6373 |
| | MCF-10A | Human normal breast cell line; ATCC No. CRL 10317 |
| | MCF7 | Human breast cancer cell line; ATCC No. HTB-22 |
| | MDA-231 | Human breast cancer cell line; ATCC No. HTB-26 |
| | MDA-4355 | Human breast cancer cell line; ATCC No. HTB-129 |

D. Vectors

| | | |
|---|---|---|
| | BK | BK virus-based episomal vector (BK shuttle episomal vector) |
| | BK-TK | A vector comprising the HTK cDNA cloned into BK shuttle episomal vector |
| | BK-UTK | A vector comprising the HTK cDNA preceeded by 650 bases of 5' UTR of rat fibroblast growth factor-2 and cloned into BK shuttle episomal vector |

E. Transfected Cell Lines

| | | |
|---|---|---|
| | [cell line] - TK | Cells transfected with BK-TK |
| | [cell line] - UTK | Cells transfected with BK-UTK |
| | [cell line] - TK/4E-AS | Cells transfected with BK-TK and with a vector transcribing e1F4E antisense RNA |
| | [cell line] - UTK/4E-A | Cells transfected with BK-UTK and with a vector transcribing e1F4E antisense RNA |

EXAMPLE 1

Plasmids and Transfection of Cell Lines

A 3 kb XhoI-SpeI fragment (described in S. L. McKnight, Nucl. Acid. Res. vol. 8: 5949–5964 (1980)) containing the herpes simplex virus type-1 thymidine kinase (HTK) cDNA was cloned into BK-Shuttle episomal vector (as shown in mammary carcinoma line). Unless otherwise stated, all cell lines were purchased the cells from the American Type Culture Collection ("ATCC"), Manassas, Va. To overexpress eIF4E (referred to as eIF4E-S, for "sense"), the eIF4E cDNA was cloned into KpnI and NotI sites of the pREP7 episomal vector (Invitrogen, Carlsbad, Calif.). To reduce the eIF4E expression (referred to as eIF4E-AS, for "antisense"), an antisense eIF4E construct was subcloned into the pREP7 vector as described in A. De Benedetti et al., "Expression of antisense RNA against initiation factor eIF-4E mRNA in HeLa cells results in lengthened cell division times, diminished translation rates, and reduced levels of both eIF-4E and the P220 component of eIF-4F," Mol. Cell. Biol., vol. 11, pp. 5435–5445 (1991).

All transfections were performed with the GenePORTER reagent (Gene Therapy Systems, San Diego, Calif.). Stable cell lines were obtained by selection with G418 for the BK constructs, and Hygromycin B for the pREP7 vectors.

EXAMPLE 2

Expression of HTK in Normal and Cancer Cell Lines

The BK-TK and the BK-UTK vectors were stably transfected into cells from both the MM3MG normal mouse mammary and the MM2MT mouse mammary carcinoma cell lines.

Figure 2A:
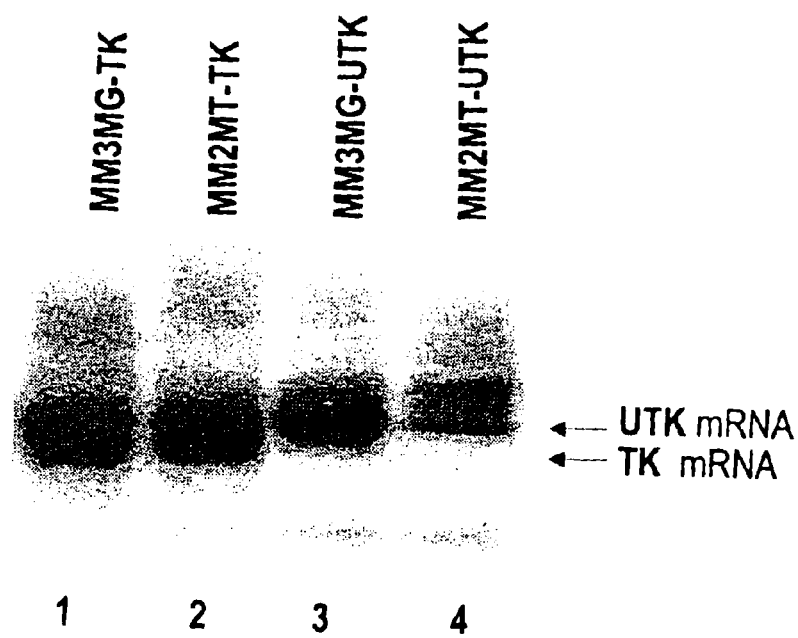
FIG. 2a illustrates a Northern blot of HTK mRNA as expressed in a normal mouse cell line (MM3MG) and a cancer mouse cell line (MM2MT) after the cells were transfected with either the BK-TK (Lanes 1 and 2) or the BK-UTK (Lanes 3 and 4) vectors.
Figure 2B:
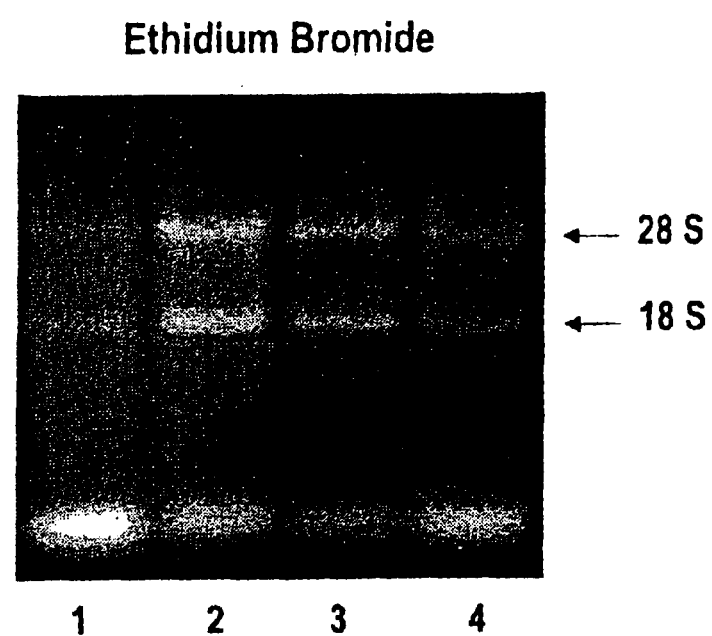
FIG. 2b illustrates the same Northern blot as in FIG. 2a, normalized for differences in RNA loading by staining with ethidium bromide.
Figure 3:
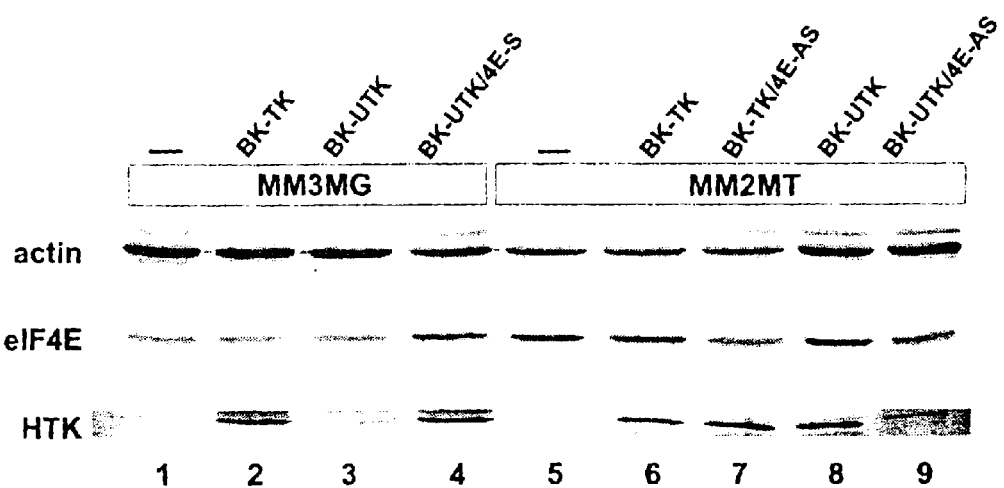
FIG. 3 illustrates a Western blot analysis of the expression of HTK protein, actin, and eIF4E as expressed in a normal mouse cell line (MM3MG) and a cancer mouse cell line (MM2MT), either in untransfected cells (Lanes 1 and 5) or in cells transfected with the BK-TK (Lanes 2 and 6) or the BK-UTK (Lanes 3 and 8) vector, or transfected with one of the previous vectors and co-transfected with an eIF4E expression vector (Lanes 4, 7 and 9).

Northern blot analyses were performed by fractionating 15 μg of total RNA on a 1.5% agarose gel, and then probing with $^{32}$P-labeled HTK cDNA (as described in S. L. McKnight, Nucl. Acid Res. vol. 8, pp. 5969–5964 (1980)). (FIG. 2a) To control for differences in RNA loading between lanes, the gel was also stained with ethidium bromide. (FIG. 2b). FIG. 2b shows that the expression of HTK mRNA was equivalent in each cell line, irrespective of the presence or absence of the 5' UTR, after adjusting for RNA loading. A different result was obtained when expression of the HTK protein was analyzed by Western blot. For the Western blot analysis, 20 μg of total protein from each sample was electrophoresed on a 10% SDS-PAGE gel, transferred to Immobilon-P membranes (Millipore, Bedford, Mass.) and probed with either anti-eIF4E , anti-actin (Sigma Chemical Co., St. Louis, Mo.) or anti-HTK rabbit sera (B. Roizman, University of Chicago, Chicago, Ill.). Robust HTK expression was seen in MM3MG normal cells transfected with the BK-TK vector, but only minimal (at least 12-fold less; p<0.00003) expression from the BK-UTK vector (FIG. 3, lanes 2 and 3). In contrast, the MM2MT cancer cells transfected with either vector showed similar expression of HTK protein (lanes 6 and 7). No HTK immunoreactive band was seen in the untransfected cells (lanes 1 and 5). The expression of eIF4E was 4-fold higher in MM2MT than that in MM3MG, after normalization by comparison to actin expression. This indicates that the expression of HTK was under translational regulation, and that elevated eIF4E in the cancer cells may allow them to overcome the inhibitory effect of the 5' UTR.

To establish that the differential synthesis of HTK protein from UTK mRNA was largely a direct consequence of the level of eIF4E, the MM3MG-UTK cells were co-transfected with an eIF4E expression vector (FIG. 3, lane 4). The level of eIF4E increased 2.25-fold as compared to parental cells (p<0.03), which resulted in a corresponding increase in HTK protein, comparable to that expressed in the MM3MG-TK cells (p<0.001). In addition, the MM2MT-TK and MM2MT-UTK cell lines were transfected with a vector transcribing eIF4E antisense RNA (FIG. 3, lanes 7 and 9). This resulted in a 2-fold reduction in the level of eIF4E in these cell lines as compared to the parental cells (p<0.05). The reduction of eIF4E in the MM2MG-TK/4E-AS cells had only a minimal effect on the synthesis of HTK (lane 7). However, synthesis of the HTK protein was reduced 13-fold in the MM2MT-UTK/4E-AS cells (p<0.0003) (lane 9). These results confirmed that the translation of UTK mRNA was strongly dependent on elevated eIF4E.

EXAMPLE 3

Selective Sensitivity of the HTK-Transfected Cells to GCV

All the MM3MG- and MM2MT- derived cell lines, prepared as described in Examples 1 and 2 and as listed below in Table 2, were incubated with various concentrations of ganciclovir ("GCV") (0.01–1000 mM) for 14 days, after which cell viability was determined. A dose-response curve showed that the MM3MG-TK (normal) cells were sensitive to low concentrations of GCV (0.1 mM), while the untransfected cells were non-specifically inhibited only at a much higher concentration (200 mM). Most importantly, the sensitivity of MM3MG-UTK cells to GCV was similar to that of the untransfected cells, reflecting the low expression of HTK in these cells. Overexpressing eIF4E in MM3MG-UTK/4E-S cells greatly increased their sensitivity to GCV. A summary of the toxic effects, expressed as the concentration of the drug that kills 50% of the cells, the Effective Dose$_{50}$ ("ED$_{50}$"), as well as the levels of eIF4E and HTK expression in each cell line as compared to a control cell line are provided in Table 2. Additionally, in Table 2, is shown the Selective Index which was calculated by dividing the ED$_{50}$ of each cell line by the ED$_{50}$ of the control, MM3MG.

A different result was obtained with MM2MT (cancer) cells. The ED$_{50}$ revealed that the MM2MT-TK cells and MM2MT-UTK were killed at nearly the same low concentration of GCV (Table 2). However, when the level of eIF4E was reduced with antisense RNA (MM2MT-UTK/4E-AS), the cells became resistant to a 370-fold higher concentration of GCV, confirming that the level of eIF4E modulates the translation of the UTK mRNA. In contrast, the MM2MT-TK/4E-AS cells were sensitive to the same concentration of GCV as the parental MM2MT-TK.

TABLE 2

Toxic Effects of GCV on Various Cell Lines

| Cell Line | ED$_{50}$ (uM) | Selective Index | eIF4E Level Relative To MM3MG $\bar{x}$ ± S.D. | HTK Level Relative To MM3MG-TK $\bar{x}$ ± S.D. |
|---|---|---|---|---|
| MM3MG | 200 | N/A | 1.0 | N/A |
| MM3MG-TK | 0.3 | 667 | 0.81 ± 0.1 | 100 |
| MM3MG-UTK | 75 | 2.7 | 0.83 ± 0.1 | 8.32 ± 2 |
| MM3MG-UTK/4E-AS | 0.9 | 222 | 3.3 ± .12 | 111.3 ± 22 |
| MM2MT | 95 | N/A | 4.2 ± .18 | N/A |

TABLE 2-continued

Toxic Effects of GCV on Various Cell Lines

| Cell Line | $ED_{50}$ (uM) | Selective Index | eIF4E Level Relative To MM3MG $\bar{x} \pm$ S.D. | HTK Level Relative To MM3MG-TK $\bar{x} \pm$ S.D. |
|---|---|---|---|---|
| MM2MT-TK | 0.095 | 1000 | 4.5 ± .17 | 122 ± 25 |
| MM2MT-TK/4E-AS | 0.15 | 633 | 1.8 ± .12 | 98.4 ± 13 |
| MM2MT-UTK | 0.5 | 190 | 4.2 ± 0.1 | 122.8 ± 25 |
| MM2MT-UTK/4E-AS | 55 | 1.7 | 1.9 ± 0.12 | 11.6 ± 4 |

EXAMPLE 4

HTK Expression and GCV Sensitivity in Human Breast Cells

Figure 4:
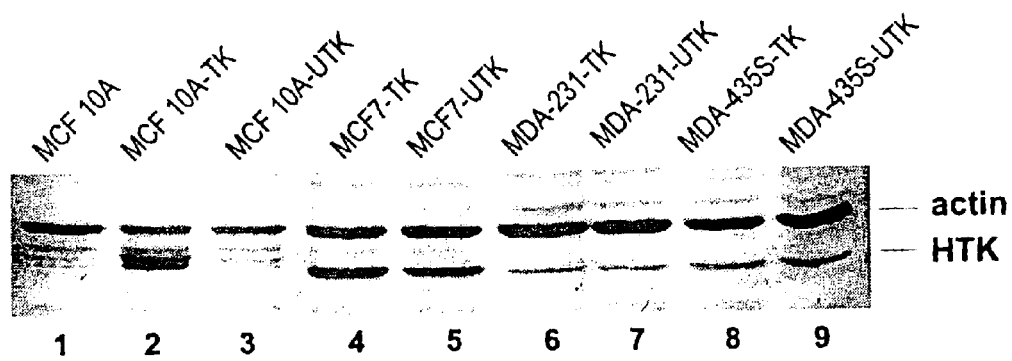
FIG. 4 illustrates a Western blot analysis of the expression of HTK protein and actin in a normal human breast cell line (MCF-10A) and three human breast cancer cell lines (MCf7, MDA-231, MDA-435S), either in untransfected cells (Lane 1) or in cells transfected with the BK-TK (Lanes 2, 4, 6, and 8) or BK-UTK (Lanes 3, 5, 7 and 9).

Since some cells are intrinsically more resistant than others to HTK/GCV, an experiment was conducted to determine if the selective killing of cancer cells could be duplicated in a panel of human breast cell lines. One normal breast cell line (MCF-10A) (ATCC No. CRL 10317) and three human breast cancer cell lines (MCF7 (ATCC No. HTB-22), MDA-231 (ATCC no.HTB-26), MDA-435S (ATCC no. HTB-129) were transfected with both the BK-TK and the BK-UTK vectors as described above in Examples 1 and 2. These cancer cell lines have a 3-fold higher level of eIF4E than the MCF-10A normal cells and 10-fold higher than a primary culture of normal breast epithelial cells. See B. Anthony et al., "Overexpression of the protooncogene-translation factor eIF-4E in breast carcinoma cell lines," Int.J.Cancer, vol. 65, pp. 858–863 (1995), and additional data not shown. To assay for the normalized expression of HTK, a Western blot was run with anti-actin and anti-HTK on samples prepared as described above in Example 2. FIG. 4 shows the expression of HTK in each cell line and the corresponding actin level. MCF-10A transfected with BK-UTK was the only cell line that showed a drastically lower synthesis of HTK.

An experiment was then conducted to determine if the differential expression of HTK in the BK-UTK vector in cancer cells rendered the cells more susceptible to GCV-mediated cell killing than were normal cells. All of the cell lines were incubated with various concentrations of GCV (0.001–10 mM) for 14 days, and cell viability was then determined. Table 3 shows that the MCF-10A-TK cells were killed at 0.3 mM GCV, but that the MCF-10A-UTK cells were no more sensitive to GCV than the untransfected MCF-10A parental cells. In contrast to MCF-10A, MCF7 cells transfected with either BK-TK or BK-UTK were both killed at similar, low GCV concentrations (0.02 and 0.01 mM, respectively), with selective indices of 300 and 600 (Table 3). This corresponds well to the expression of HTK (FIG. 4, lanes 4, 5). The same was true for MDA-435S cells (Table 3).

These data illustrate that cancer cell lines can generally synthesize HTK equally well from either the BK-TK or BK-UTK vectors. However, an anomaly was seen in the MDA-231 cells. Although both the MDA-231-TK and MDA-231-UTK cells synthesized HTK equally well (FIG. 4, lanes 6, 7), the cells were insensitive to GCV, except for non-specific toxicity at 5 mM (Table 3). Although this result was unexpected, similar results and variability in GCV sensitivity have previously been reported. See C. Beck et al., "The Thymidine Kinase/Ganciclovir-Mediated 'Suicide' Effect Is Variable in Different Tumor Cells," Human Gene Therapy, vol.6, pp.1525–1530 (1995). One possibility is that these cells may display multi-drug resistance, rendering them insensitive to GCV. In fact, the patient from whom this cell line had been isolated had been treated with adriamycin, and may have become resistant to GCV.

TABLE 3

Toxicity of GCV

| Cell Line | $ED_{50}$ (mM) | Selective Index | HTK Level Relative To MCF 10A-TK (%) $\bar{x} \pm$ S.D. |
|---|---|---|---|
| MCF-10A | 6.0 | N/A | N/A |
| MCF-10A-TK | 0.3 | 20.0 | 100 |
| MCF-10A-UTK | 5.5 | 1.1 | 1.5 ± 0.1 |
| MCF7 | 6.0 | N/A | N/A |
| MCF7-TK | 0.02 | 300 | 82 ± 10 |
| MCF7-UTK | 0.01 | 600 | 87 ± 20 |
| MDA-231 | 6.0 | N/A | N/A |
| MDA-231-TK | 4.0 | 1.5 | 46 ± 13 |
| MDA-231-UTK | 4.0 | 1.5 | 49 ± 9 |
| MDA-435S | 0.35 | N/A | N/A |
| MDA-435S-TK | 0.015 | 23.3 | 53 ± 20 |
| MDA-435S-UTK | 0.015 | 23.3 | 57 ± 20 |

EXAMPLE 5

Tumor Ablation in Mice

To test for regression of primary tumors by local injection of the vectors followed by systemic treatment with GCV, MM2MT (cancer) cells were injected into the mammary fat pad of three-week-old female BALB/c athymic nu/nu mice, purchased from Harlan Sprague Dawley (Indianapolis, Ind.). $10^6$ MM2MT cells were suspended in 0.1 ml serum and antibiotic-free DMEM medium and injected subcutaneously into the mammary fat pad. Tumor latency was determined as the time necessary for the tumors to grow to 0.5 cm (largest diameter). Tumor doubling times were determined by daily measuring the smallest (d) and the largest (D) diameters with calipers, and estimating the volume using the formula, $V=D \times d^2 \times 0.52$. The reported numbers are the mean and standard deviation of the tumor volumes for each group.

When the tumor volumes were approximately 40 mm³, the mice were randomly separated into two groups, and either the BK-TK or the BK-UTK vectors were injected as a liposomal complex near the tumor. To make the liposomal complex for transfection of primary tumors, 10 mg of endotoxin-free purified (QIAGEN, Inc., Valencia, Calif.)

plasmid DNA was diluted in 50 ml medium without serum or antibiotics. In a separate tube, 50 ml of GenePORTER reagent (Gene Therapy Systems, San Diego, Calif.) was mixed with 50 ml serum and antibiotic-free medium. The two tubes were then combined, briefly vortexed, and allowed to incubate at room temperature for 20 minutes, after which the resulting liposome complex was injected between the tumor and the skin of the mouse.

Figure 5:
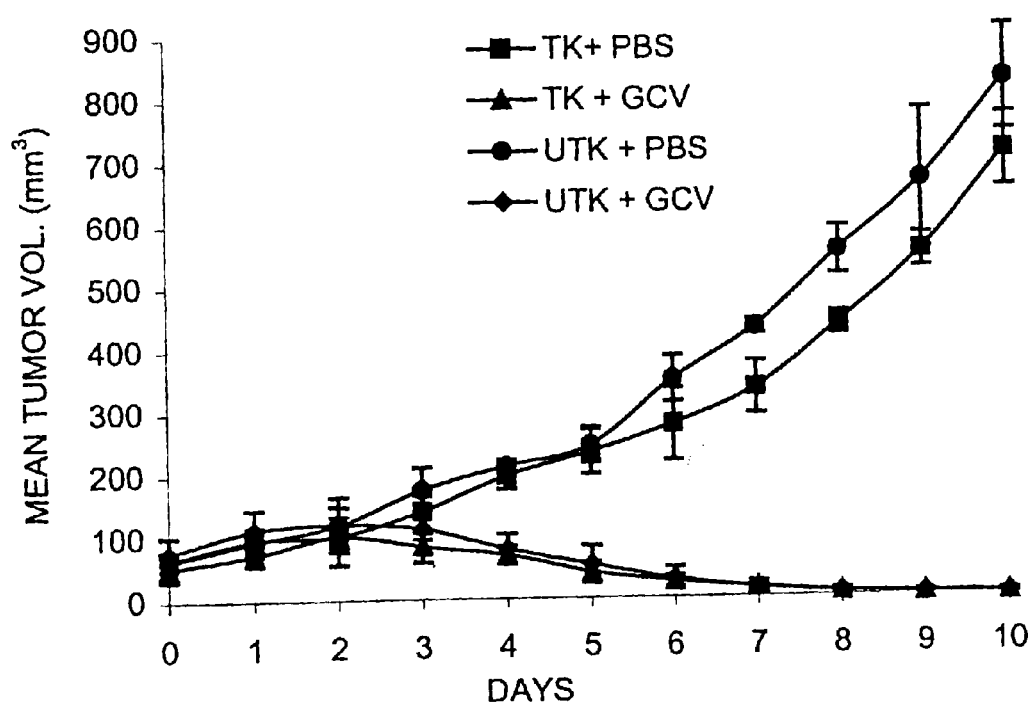
FIG. 5 illustrates the change in tumor volume over time in mice injected with MM2MT cancer cells to form tumors that were allowed to grow to an initial volume of 40 mm$^3$, subsequently injected with either the BK-TK or BK-UTK vectors, and then treated with a placebo (PBS) or with ganciclovir (GCV).

Two days after the vectors were injected, the BK-TK group (N=9) and the BK-UTK group (N=9) were each randomly separated into two groups of 3 mice (PBS control) and 6 mice (GCV experiment). Each group was then treated with a single intraperitoneal dose of either 100 mg/kg GCV or 200 ml PBS each day for a total of 10 days. FIG. 5 shows that while the tumor volumes continued to increase in the control groups (PBS treatment), there was substantial tumor reduction in both the BK-TK and the BK-UTK groups of mice treated with GCV. One of the 6 mice in each group had no palpable tumor remaining at the end of the 10-day treatment. Between the transfected groups, a significant difference ($P<0.001$) in the mean tumor volume was found in the mice that received GCV treatment versus the PBS control. In previous experiments we had verified that GCV had no effect on the growth of MM2MT tumors when administered alone (data not shown).

Figure 6:
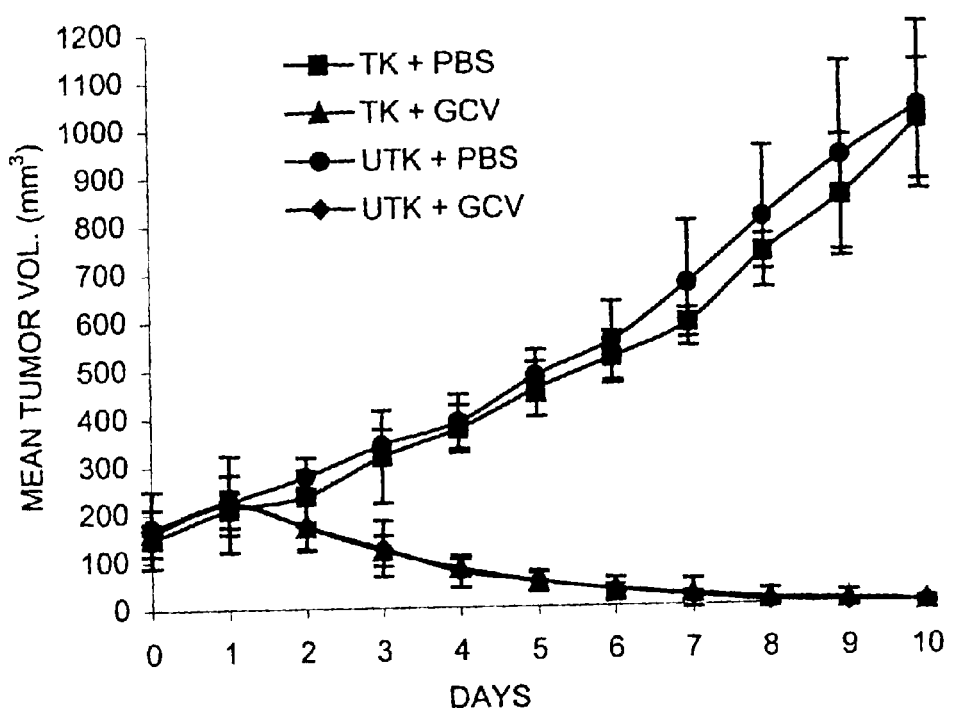
FIG. 6 illustrates the change in tumor volume over time in mice injected with MM2MT cancer cells to form tumors that were allowed to grow to an initial volume of 100 mm$^3$, subsequently injected with either BK-TK or BK-UTK vectors, and then treated with a placebo (PBS) or with ganciclovir (GCV).

Since the "bystander effect", defined as an immune response elicited by dying cancer cells, is known to play a role in the HTK/GCV system, attempts to cause ablation of even larger tumors in immunocompetent mice were tried. MM2MT cells were injected into the mammary fat pad of 18 BALB/c white mice. When the tumor volumes were at least 100 mm$^3$, the mice were randomly separated into two groups, one group receiving the BK-TK vector (N=9) and the other group the BK-UTK vector (N=9). In both groups, the vector was introduced into the tumor via liposomal delivery, as described above. As with the previous experiment, two days after delivery of the vectors, both the BK-TK and the BK-UTK groups were randomly separated into 2 groups of 3 mice (PBS control) and 6 mice (GCV treatment), with each group receiving a daily injection of either 100 mg/kg GCV or 200 ml PBS for a total of 10 days. When the GCV treatment began, the tumor volumes were approximately 150 mm$^3$. While tumor volumes in the control (PBS) groups continued to grow (FIG. 6), all of the tumors in both the BK-TK ($P<0.0002$) and the BK-UTK ($P<0.0008$) groups that were treated with GCV substantially regressed. In fact, 4 of the 6 mice in the BK-TK group, and 2 of the 6 mice in the BK-UTK group no longer had palpable tumors at the end of the experiment.

EXAMPLE 6

Toxicity of the BK-TK and the BK-UTK Vectors Following Systemic Delivery

As shown in Examples 2 and 3, translation of the UTK mRNA is inhibited in normal cell lines, but not in cancer cells, producing only minimal sensitivity to GCV in the normal cell lines stably transfected with the BK-UTK vector. However, to help exclude the possibility that the UTK mRNA produced from the BK-UTK vector could be translated in some normal tissues, we determined the toxicity of the BK-UTK vector as compared to that of the BK-TK vector following in vivo systemic administration.

To deliver the vectors systemically, 100 mg of plasmid DNA was diluted in 150 ml of medium. In a separate tube, 400 ml of GenePORTER reagent was mixed with 150 ml of medium. After mixing as above, the liposome complex was injected in the lateral tail veins of three mice. To verify that the vectors were successfully delivered in the liposomal complex to various organs, two days after injection of the vectors the mice were sacrificed and the following tissues were removed to prepare a supernatant for vector recovery: brain, heart, colon, kidney, liver, lung, spleen, and thymus. See B. Hirt, "Selective extraction of polyoma DNA from infected mouse cell cultures," *J. of Mol. Biol.*, vol. 26, pp. 365–369 (1967). Purified DNA was then quantified and subjected to PCR analysis using primers flanking regions of the BK-Shuttle multiple cloning site. A PCR product specific for the vector was detected in all tissues, confirming efficient systemic transfection (data not shown). An untransfedted mouse was used as a negative control.

Additional BALB/c white mice were weighed and injected in the lateral tail vein with a liposomal complex containing either 100 mg of the BK-Shuttle (empty vector control), the BK-TK, or the BK-UTK. Two days later, all mice received an intraperitoneal injection of 100 mg/kg/day of GCV for a total of 10 days. Table 4 shows that 2 of the 6 mice that received the BK-TK vector died before the end of the experiment (3 and 6 days after GCV treatment began). However, no mice expired in either the control group or the BK-UTK group during GCV treatment. In addition, the mean weight of the surviving BK-TK mice decreased by 10% by the end of the experiment, in contrast to the 15% and 16% increases in the mean weights of the vector control and BK-UTK group of mice, respectively.

Besides weight loss, the mice in the BK-TK group showed other signs of morbidity, including lethargy, lack of grooming, and ruffled fur, none of which were seen in either the control or the BK-UTK groups. Additionally, the intestines of three of the mice from the BK-TK group were found to be dark and necrotic. This finding was in stark contrast to the healthy intestines found in mice that received either the BK-Shuttle or the BK-UTK.

At the end of the 10 days, selected organs from each mouse were weighed, and the weights were normalized by expressing them as a percentage of the mouse's body weight. These percentages for each organ were then expressed as a mean percentage of total body weight for each group with the corresponding standard error. The results for spleen and liver, the organs with the greatest changes, are reported in Table 4; the thymus also shrunk significantly in the BK-TK group, although it is not believed that this contributed to morbidity. Overall, the results showed very little difference between the BK-Shuttle and the BK-UTK groups, indicating little or no systemic toxicity due to the BK-UTK vector and GCV treatment.

In contrast, there were substantial reductions in the mean organ weight percentages of the BK-TK mice. The mean weight percentages of the thymus and the spleen of the BK-TK mice were only 25% ($P<0.0003$) and 43% ($P<0.003$) of those of the control mice, respectively. To a lesser extent, the mean liver and kidney percentages were reduced, to 70% ($P<0.03$) and 75% ($P<0.02$) of those of the control mice, respectively. Note that the observed toxicity was not due to GCV alone, since no effects were seen in the BK-Shuttle group.

TABLE 4

Changes in Weight in BALB/c Mice Following Systemic Administration of Vector and Treatment with GCV

| Vector | Deaths During GCV Treatment | Starting Weight $\bar{x} \pm$ S.D. (gm) | Ending Weight $\bar{x} \pm$ S.D. (gm) | Percent Weight Change | Percent Change in Mean Spleen Weight/Mean Body Weight | Percent Change in Mean Liver Weight/Mean Body Weight |
|---|---|---|---|---|---|---|
| BK-Shuttle | 0/3 | 14.4 ± 0.6 | 16.5 ± 0.5 | 15% Increase | No Change | No Change |
| BK-TK | 2/6 | 15.5 ± 0.9 | 14.1 ± 0.5 | 10% Decrease | 57% Decrease | 30% Decrease |
| BK-UTK | 0/6 | 15.4 ± 1.3 | 17.9 ± 1.3 | 16% Increase | No change | No Change |

EXAMPLE 7

Effect of the BK-TK and the BK-UTK Vectors on Metastatic Tumor Burden and Survival Since the BK-UTK vector had little toxicity when administered systemically, the next step was to determine whether this vector could be an effective therapy for metastasis. 50 BALB/c white mice were weighed prior to injection with cells. $10^5$ MM2MT cells were suspended in 150 ml of medium and injected into the lateral tail vein of each mouse. In preliminary experiments, upon sacrificing mice every 6 days, visible lung nodules had been found to appear in about 18 days (data not shown). Thus, eighteen days after the cells were injected, the mice were randomly placed into three groups: 20 mice were injected intravenously with 100 mg of the BK-TK vector liposomal complex, 20 mice were injected with 100 mg of the BK-UTK vector liposomal complex, and 10 mice were not injected (control). Two days after injection of the vectors, 100 mg/kg/day of GCV was administered intraperitoneally to 10 mice each from both the BK-TK group and the BK-UTK group. The other 10 mice from each group, as well as the control group, received a daily intraperitoneal injection of 200 ml PBS. After 10 days of treatment, all mice were sacrificed. The lungs were removed and stained with Bouin's solution. The number of lung metastases were counted using a dissecting microscope. Mice were only sacrificed before the end of the experiment if they became moribund. The results of this experiment are summarized below and in Table 5.

The control mice and those that had received the BK-TK and BK-UTK vectors followed by PBS had a large number of lung metastases, with means ranging from 41.8 to 46.6. There was no statistically significant difference in the mean numbers of tumors in the mice that received either the BK-TK or the BK-UTK vector followed by PBS versus the control mice (MM2MT group). In contrast, the group of mice that received either the BK-TK or BK-UTK vectors and GCV had a significantly lower mean number (3) of lung metastases ($P<0.01$, compared to the control group). Importantly, 7 mice in the BK-TK group and 4 mice in the BK-UTK group receiving GCV had no visible lung metastasis on inspection (Table 5). Finally, all but one group of mice exhibited an increase in mean weight, including a 16% increase in the mice treated with the BK-UTK vector and GCV. The exception was the BK-TK group treated with GCV, which showed a 15% decrease in mean weight. In addition, the BK-TK group was the only one in which any mice had to be sacrificed before the end of the 10 day treatment with GCV (3 of 10 mice) due to their moribund state.

TABLE 5

Summary of Metastasis Experiments

| Group (N = 10) | Starting Weight (gm) $\bar{x} \pm$ S.D. (range) | Ending Weight (gm) $\bar{x} \pm$ S.D. (range) | Percent Weight Change | Deaths During GCV Treatment | Number Lung Tumors x (range) | Number Without Lung Tumors |
|---|---|---|---|---|---|---|
| MM2MT (PBS) | 15.86 ± 1.3 (13.92–17.51) | 19.64 ± 2.8 (12.77–21.35) | 24% Increase | 0 | 46.6 (4–98) | 0 |
| MM2MT (TK + PBS) | 15.78 ± 1.1 (13.79–17.32) | 18.89 ± 2.5 (14.4–20.95) | 20% Increase | 0 | 41.8 (15–132) | 0 |
| MM2MT (TK + GCV) | 16.45 ± 1.1 (14.9–18.5) | 13.61 ± 3.4 (9.35–18.47) | 15% Decrease | 3 | 3.1* (0–7) | 7 |
| MM2MT (UTK + PBS) | 15.75 ± 1.3 (13.45–17.11) | 18.33 ± 2.1 (13.43–20.66) | 16% Increase | 0 | 42.8 (11–89) | 0 |
| MM2MT (UTK + GCV) | 15.95 ± 1.1 (13.8–17) | 18.58 ± 2.2 (13.44–21.28) | 16% Increase | 0 | 3.0** (0–13) | 4 |

*P < 0.01 as compared to the MM2MT control group (no vector, only PBS)
**P < 0.02 as compared to the MM2MT control group (no vector, only PBS)

EXAMPLE 8

Effect of the BK- TK and the BK- UTK Vectors on Long-Term Survival

Figure 7:
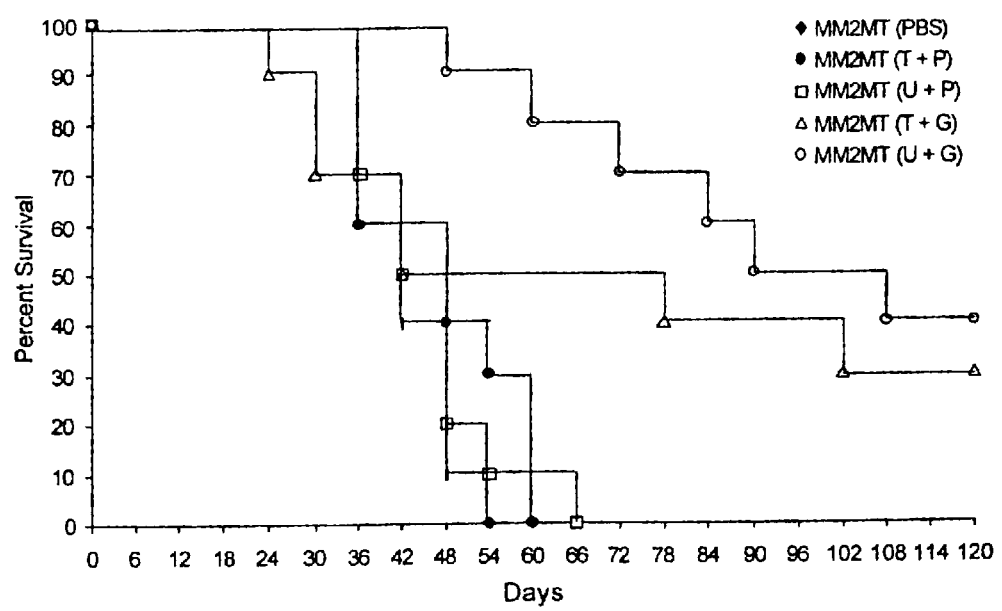
FIG. 7 illustrates a Kaplan-Meier 120 day survival analysis for mice injected with MM2MT cancer cells to form tumors, subsequently injected with either BK-TK or BK-UTK vectors, and then treated with a placebo (PBS) or with ganciclovir (GCV).

The metastasis experiment described above was repeated to determine whether this therapy would increase the long-term survival of the mice. Instead of sacrificing the mice after ten days of treatment (i.e., a total of thirty days after the initial injection of MM2MT cells), the experiment was extended to a total of 120 days. The mice were sacrificed before the end of the experiment only if they became moribund. FIG. 7 is a Kaplan-Meier graph (see C. O. Nathan et al., "Analysis of surgical margins with the molecular marker eIF4E: a prognostic factor in patients with bead and neck cancer," *J. Clin. Oncology*, vol. 17, pp. 1–6 (1999)), showing the survival of the various groups of mice and Table 6 summarizes the results of the experiment.

The mice that were treated with PBS had a mean survival of 42 days; the mice treated with the BK-TK vector and GCV had a mean survival of 60 days; and the mice treated with the BK-UTK vector and GCV had a mean survival of 96 days. (Table 6) Most importantly, there was a 64% increase in the mean survival of the BK-UTK mice that received GCV compared to the BK-TK mice that received the same treatment. Only the mice in the BK-UTK group treated with GCV had a statistically significant increase in the mean length of survival compared to the MM2MT control group of mice (P<0.0001). Note that the BK-TK group of mice that were treated with GCV was the only group in which moribund mice had to be sacrificed before the end of the ten-day treatment with GCV (three often mice). The mice that survived for the duration of the experiment (120 Days) were sacrificed, and no evidence of tumors in any organ was found in any of these mice.

assess eradication of metastases. Perhaps, repeated injections of the vector to ensure greater tissue coverage, and a longer GCV treatment could result in a more effective cure.

The term "therapeutically effective amount" as used herein refers to an amount of a selected DNA sequence that is sufficient to inhibit metastatic tumor growth in a mammal, such DNA sequence comprising a constitutive promoter operatively linked to a transcription sequence; wherein the transcription sequence, when transcribed, produces a messenger RNA sequence that comprises a translatable sequence encoding a toxin, and an untranslated sequence; wherein the untranslated sequence inhibits translation of the toxin sequence in the absence of eukaryotic initiation factor eIF4E, and wherein the untranslated sequence allows translation of the toxin sequence into a toxin in the presence of eukaryotic initiation factor eIF4E. The term "therapeutically effective amount" therefore includes, for example, an amount of such selected DNA sequence sufficient to prevent the growth of the patient's tumor, and preferably to reduce by at least 50%, and more preferably to reduce by at least 90%, the mass of a patient's tumor. The dosage ranges for the administration of the selected DNA sequence are those that produce the desired effect. Generally, the dosage will vary with the age, weight, condition, sex of the patient, type of tumor, and degree of tumor development. A person of ordinary skill in the art, given the teachings of the present specification, may readily determine suitable dosage ranges. The dosage can be adjusted by the individual physician in the event of any contraindications. In any event, the effectiveness of treatment can be determined by monitoring the extent of tumor growth and remission by methods well known to those in the field.

The complex 5'UTR used as a promoter for translation in this application is such that by placing this complex 5'UTR in front of the open reading frame of the toxin or conditional

TABLE 6

Summary of Survival Study

| Group (N = 10) | Number Dead Before 30 Days | Number Surviving 120 Days | Mean Length of Survival (Days) | Percent Increased Mean Survival Over MM2MT (PBS) | Percent Increased Mean Survival Over MM2MT (TK-GCV) |
|---|---|---|---|---|---|
| MM2MT (PBS) | 0 | 0 | 41.0 | | N/S |
| MM2MT (TK-PBS) | 0 | 0 | 43.0 | 5% | N/S |
| MM2MT (UTK + PBS) | 0 | 0 | 42.5 | 4% | N/S |
| MM2MT (TK + GCV) | 3 | 3 | 58.5 | 43% | |
| MM2MT (UTK + GCV) | 0 | 4 | 96.0* | 134% | 64% |

*P < 0.0001 compared to MM2MT (PBS) group;
N/S = Not significant

A viral vector system could also be used in lieu of the episome construct. Liposomal delivery was chosen in the initial embodiment because of the ease and low cost of preparing large amounts of plasmid. This system allowed efficient delivery of the vector to a large number of tissues with little to no adverse effects following GCV treatment. Hence, translational regulation of HTK or other toxin expression can potentially be used to treat wide variety of cancers. We were able to prolong the life span of mice already bearing a large number of metastases with no adverse effects. Note that only a single injection of the vector was employed, and only ten days of GCV therapy to toxin, only cells that have higher levels of eIF4E and hence increased helicase activity, are able to continue to translate this hybrid mRNA. In one embodiment, we used the 5'UTR of basic fibroblast growth factor (FGF-2), an angiogenic factor previously found to be translationally regulated by eIF4E. See Kevil et al., 1995. However, other complex hairpin sequences could be used for translational enhancement by eIF4E, e.g., untranslated hairpin sequences on genes of the proto-oncogene c-myc, cyclin D1, ornithine decarboxylase, or vascular endothelial growth factor ("VEGF") (otherwise known as vascular permeability factor ("VPF")) genes. It is preferred that the UTR sequence comprise a natural or synthetic hairpin conformation with a stability of at least about $\Delta G \geq 50$ Kcal/mol. To achieve this stability and thus a tight hairpin formation, a relatively long palindromic oligonucleotide sequence that is self-complementary is required. See A. E. Koromilas et al., "mRNAs containing extensive secondary structure in their 5' non-coding region translate efficiently in cells overexpressing initiation factor eIF-4E," The EMBO Journal, vol. 11, pp. 4153–4158 (1992); and A. DeBenedetti et al., 1999.

Toxins Suitable for Use in the Present Invention

In addition to the HTK gene, genes encoding any of a number of other toxins may also be used in the present invention. The HTK gene product is conditionally lethal, as that product is an enzyme that converts ganciclovir into a toxin. (Other toxins that could be used in this invention are discussed below.) As used in the specification and claims, a "toxin" may either be a molecule that is directly toxic to a cell expressing the molecule, or a molecule that is conditionally toxic, e.g., one that depends on the presence of a co-factor (e.g., ganciclovir) for toxicity.

Preferably, a toxin should have the following characteristics:

(1) The toxin should be capable of being readily produced under the regulatory control of a promoter, i.e., a peptide or protein. For example, a suitable toxin may be one of the many toxic peptides known in the art.

(2) The toxin should kill only the cell in which it is expressed, and not neighboring cells.

There are numerous toxins from plants, animals, and bacteria satisfying these criteria. For example, there are many bacterial toxins that use an A/B subunit motif, in which the A subunit is toxic once it enters a cell but has no ability to cross cell membranes unassisted, and in which the B subunit (or multi-subunit complex) binds to cells but has no toxicity on its own. The A subunit, even when injected systemically, is non-toxic. See, e.g., Balfanz, L., Rautenberg, P., and U. Ullmann. 1996. Molecular mechanisms of action of bacterial exotoxins. Zbl. Bakt. 284: 170–206.; Middlebrook, J. L. and R. B. Dorland. 1984. Bacterial toxins: cellular mechanisms of action. Microbiological Reviews. 48: 199–221. Nucleic acids coding for the A or active subunit could be used in this invention because the A subunit will already be inside the cell when it is produced, so it will not be necessary to include sequences coding for the B or cell-binding component. The A subunit will kill the cell in which it is expressed, but will not damage other cells when released by cell lysis because the A subunit could not gain access to the interior of other cells. Examples include the A subunit of cholera toxin, which destroys ion balance, and the A subunit of diphtheria toxin, which terminates protein synthesis. Other toxins comprise a single peptide chain having separate domains, where one domain functions to enable entry into the cell and a second domain is toxic. Such a multidomain peptide toxin could be truncated, using genetic engineering to produce a construct that only codes for the toxin domain. Use of a truncated toxin that is only expressed within target cells, and that cannot enter other cells, avoids the problem of general toxicity with respect to nontarget cells. One example of a truncated toxin that has been used in other systems to kill artificially targeted cells is the truncated form of exotoxin A from *Pseudomonas aeruginosa*. Pastan, I., and FitzGerald, D. 1991. Recombinant toxins for cancer treatment. Science 254: 1173–1177. The commonly used ricin toxin from plants also uses this same type of A/B subunit motif. Lee, H. P. et al., "Immunotoxin Therapy for Cancer," *JAMA*, vol. 269, pp. 78–81 (1993).

With such "catalytic" toxins, very few toxin molecules—even as few as a single molecule—would need to be expressed to kill a target cell. Catalytic toxins such as diphtheria toxin A polypeptide have been successfully used (in another context) to selectively kill cell lineages in transgenic mice. See R. Palmiter et al., "Cell lineage ablation in transgenic mice by cell-specific expression of a toxin gene," *Cell*, vol. 50, pp. 435–443 (1987).

Other classes of "non-catalytic" peptide toxins may also be useful, such as the class of peptides called "lytic peptides," or "antimicrobial amphipathic peptides." These peptides are relatively small, generally containing 20 to 50 amino acids (or even fewer), and are capable of forming an amphipathic alpha helix in a hydrophobic environment, wherein at least part of one face is predominantly hydrophobic and at least part of the other face is predominately hydrophilic and is positively charged at physiological pH. Such structures can be predicted by applying the amino acid sequence to the Edmundson helical wheel (Schiffer, M., and A. B. Edmundson. 1967. Use of the helical wheel to represent the structures of proteins and to identify segments with helical potential. Biophys. J. 7:121–135.). In addition to their small size, such peptides are widely distributed in nature and vary significantly in toxicity. They can also be designed to possess different levels of lytic activity. Typically, when applied to cells in culture, a few micrograms per ml are required to kill the cells. The level of toxicity of lytic peptides is determined by the amino acid composition and sequence. Different peptides can have widely differing levels of toxicity. In addition, relatively few molecules should be needed to kill a cell if the cell produces the molecules internally. A further discussion of lytic peptides suitable for use in this invention appears below.

Cloning of Lytic Peptide Genes

Due to the role played by lytic peptides in nature, especially to protect against bacterial infections, the production of lytic peptides by various cloning technologies has been widely investigated and published. A consistent finding of workers who have attempted to express lytic peptides by cloning is that the lytic peptides kill the cells expressing the cloned lytic peptide gene, thereby seriously reducing product yields. In nature most lytic peptides are produced with signal sequences directing the product to be stored in membrane-bound vesicles, to be secreted on mucosal surfaces. Investigators have overcome this "killing problem" either by using mechanized peptide synthesizers, or by generating fusion proteins that are non-lytic until the lytic domain has been cleaved from the carrier domain.

In this context, the killing of the cell producing the cloned lytic peptide has been viewed as an unwanted consequence, resulting in failure of the experiment. By contrast, in the present invention the killing of cells that produce the cloned lytic peptide does not represent a failed experiment, but rather is the desired consequence in eliminating cancer cells.

Successful cloning and expression of various lytic peptides in cultured cells, in plants, and in animals is well documented See, e.g., Gudmundsson, G. H., Lidholm, D. A., Asling, B., Gan, R., and H. G. Boman. 1991. The cecropin locus: cloning and expression of a gene cluster encoding three antibacterial peptides in *Hyalophora cecropia*. J. Biol. Chem.266:11510–11517.; Cooperand Enright, U.S. patent application Ser. No. 08/491,609, filed Jun. 7, 1995 and affidavits submitted therein; and U.S. Pat. No. 5,556,782. Recently, genes encoding lytic peptides, under the control of promoters inducible in response to bacterial endotoxins, have been successfully cloned into catfish and shown to be functional to produce the lytic peptide in response to endotoxin. Cooper and Enright, U.S. patent application Ser. No. 08/491,609, filed Jun. 7, 1995 and affidavits submitted therein. Genes encoding lytic peptides have also been successfully genetically engineered into plants. See Hightower, R., Baden, C., Penzes, E., and P. Dunsmuir. 1994. The expression of cecropin peptide in transgenic tobacco does not confer resistance to *Pseudomonas syringe pv tabaci.* Plant Cell Rep. 13: 295–299.; Allefs, S., Florack, D. Hoogendoom, C., and W. J. Stiekeme. 1995. Erwinia soft rot resistance of potato cultivars transformed with a gene construct coding for antimicrobial peptide cecropin B is not altered. Am. Potato J. 72: 437–445; Florack, D., Allefs, S., Bollen, R., Bosch, D., Visser, B., and W. Stiekema. 1995. Expression of giant silkmoth cecropin B encoding genes in transgenic tobacco. *Transgenic Research* 4:132–141.; Jaynes, J. M., Nagpala, P., Destefano-Beltran, L., Huang, J. H., Kim, J., Denny, T., and S. Cetiner. 1993. Expression of a cecropin B lytic peptide analog in transgenic tobacco confers enhanced resistance to bacterial wilt caused by *Pseudomonas solanacearum.* Plant Sci. 89:43–53.; and U.S. Pat. Nos. 5,597,946 and 5,597,945.

Lytic Peptides Useful in the Present Invention

Many lytic peptides are known in the art and include, for example, those mentioned in the references cited in the following discussion.

Lytic peptides are small, basic peptides. Native lytic peptides appear to be major components of the antimicrobial defense systems of a number of animal species, including those of insects, amphibians, and mammals. They typically comprise 23–39 amino acids, although they can be smaller. For example, the protegrins from porcine leukocytes have 16–18 amino acids, and fragments down to 12 amino acids show activity against bacteria. See X-D Qu et al., "Protegrin Structure and Activity against *Neisseria gonorrhoea,*" *Infection and Immunity,* vol.65, pp.636–639 (1997). Some designed peptides show activity at even shorter lengths. See McLaughlin et al., cited below.

Lytic peptides have the potential for forming amphipathic alpha-helices. See Boman et al., "Humoral immunity in Cecropia pupae," *Curr. Top. Microbiol. Immunol.* vol. 94/95, pp. 75–91 (1981); Boman et al., "Cell-free immunity in insects," *Ann. Rev. Microbiol.,* vol.41, pp.103–126 (1987); Zasloff, "Magainins, a class of antimicrobial peptides from Xenopus skin: isolation, characterization of two active forms, and partial DNA sequence of a precursor," *Proc. Natl. Acad. Sci. USA,* vol. 84, pp. 3628–3632 (1987); Ganz et al., "Defensins natural peptide antibiotics of human neutrophils," *J. Clin. Invest.,* vol. 76, pp. 1427–1435 (1985); and Lee et al., "Antibacterial peptides from pig intestine: isolation of a mammalian cecropin," *Proc. Natl. Acad. Sci. USA,* vol. 86, pp. 9159–9162 (1989).

Known amino acid sequences for lytic peptides may be modified to create new peptides that would also be expected to have lytic activity by substitutions of amino acid residues that preserve the amphipathic nature of the peptides (e.g., replacing a polar residue with another polar residue, or a non-polar residue with another non-polar residue, etc.); by substitutions that preserve the charge distribution (e.g., replacing an acidic residue with another acidic residue, or a basic residue with another basic residue, etc.); or by lengthening or shortening the amino acid sequence while preserving its amphipathic character or its charge distribution. Lytic peptides and their sequences are disclosed in Yamada et al., "Production of recombinant sarcotoxin IA in *Bombyx mori* cells," *Biochem. J.,* vol. 272, pp. 633–666 (1990); Taniai et al., "Isolation and nucleotide sequence of cecropin B cDNA clones from the silkworm, *Bombyx mori,*" *Biochimica Et Biophysica Acta,* vol. 1132, pp. 203–206 (1992); Boman et al., "Antibacterial and antimalarial properties of peptides that are cecropin-melittin hybrids," *Febs Letters,* vol. 259, pp. 103–106 (1989); Tessier et al., "Enhanced secretion from insect cells of a foreign protein fused to the honeybee melittin signal peptide," *Gene,* vol. 98, pp. 177–183 (1991); Blondelle et al., "Hemolytic and antimicrobial activities of the twenty-four individual omission analogs of melittin," *Biochemistry,* vol. 30, pp. 4671–4678 (1991); Andreu et al., "Shortened cecropin A-melittin hybrids. Significant size reduction retains potent antibiotic activity," *Febs Letters,* vol. 296, pp. 190–194 (1992); Macias et al., "Bactericidal activity of magainin 2: use of lipopolysaccharide mutants," *Can. J. Microbiol.,* vol. 36, pp. 582–584 (1990); Rana et al., "Interactions between magainin-2 and *Salmonella typhimurium* outer membranes: effect of Lipopolysaccharide structure," *Biochemistry,* vol. 30, pp. 5858–5866 (1991); Diamond et al., "Airway epithelial cells are the site of expression of a mammalian antimicrobial peptide gene," *Proc. Natl. Acad. Sci. USA,* vol. 90, pp. 4596ff (1993); Selsted et al., "Purification, primary structures and antibacterial activities of β-defensins, a new family of antimicrobial peptides from bovine neutrophils," *J. Biol. Chem.,* vol. 268, pp. 664 1ff(1993); Tang et al., "Characterization of the disulfide motif in BNBD-12, an antimicrobial β-defensin peptide from bovine neutrophils," *J. Biol. Chem.,* vol. 268, pp. 6649ff (1993); Lehrer et al., *Blood,* vol. 76, pp. 2169–2181 (1990); Ganz et al., *Sem. Resp. Infect. I.,* pp. 107–117 (1986); Kagan et al., *Proc. Natl. Acad. Sci. USA,* vol. 87, pp. 210–214 (1990); Wade et al., *Proc. Natl. Acad. Sci. USA,* vol. 87, pp. 4761–4765 (1990); Romeo et al., *J. Biol. Chem.,* vol. 263, pp. 9573–9575 (1988); Jaynes et al., "Therapeutic Antimicrobial Polypeptides, Their Use and Methods for Preparation," WO 89/00199(1989); Jaynes, "Lytic Peptides, Use for Growth, Infection and Cancer," WO 90/12866 (1990); Berkowitz, "Prophylaxis and Treatment of Adverse Oral Conditions with Biologically Active Peptides," WO 93/01723 (1993).

Families of naturally-occurring lytic peptides include the cecropins, the defensins, the sarcotoxins, the melittins, and the magainins. Boman and coworkers in Sweden performed the original work on the humoral defense system of *Hyalophora cecropia,* the giant silk moth, to protect itself from bacterial infection. See Hultmark et al., "Insect immunity. Purification of three inducible bactericidal proteins from hemolymph of immunized pupae of *Hyalophora cecropia,*" *Eur. J. Biochem.,* vol. 106, pp. 7–16 (1980); and Hultmark et al., "Insect immunity. Isolation and structure of cecropin D. and four minor antibacterial components from *cecropia* pupae," *Eur. J. Biochem.,* vol. 127, pp. 207–217 (1982).

Infection in *H. cecropia* induces the synthesis of specialized proteins capable of disrupting bacterial cell membranes, resulting in lysis and cell death. Among these specialized proteins are those known collectively as cecropins. The principal cecropins—cecropin A, cecropin B, and cecropin D—are small, highly homologous, basic peptides. In collaboration with Merrifield, Boman's group showed that the amino-terminal half of the various cecropins contains a sequence that will form an amphipathic alpha-helix. Andrequ et al., "N-terminal analogues of cecropin A: synthesis, antibacterial activity, and conformational properties," *Biochem.,* vol. 24, pp. 1683–1688 (1985). The carboxy-terminal half of the peptide comprises a hydrophobic tail. See also Boman et al., "Cell-free immunity in Cecropia," *Eur. J. Biochem.,* vol. 201, pp. 23–31 (1991).

A cecropin-like peptide has been isolated from porcine intestine. Lee et al., "Antibacterial peptides from pig intestine: isolation of a mammalian cecropin," *Proc. Natl. Acad. Sci. USA*, vol. 86, pp. 9159–9162 (1989).

Defensins, originally found in mammals, are small peptides containing six to eight cysteine residues. Ganz et al., "Defensins natural peptide antibiotics of human neutrophils," *J. Clin. Invest.*, vol. 76, pp. 1427–1435 (1985). Extracts from normal human neutrophils contain three defensin peptides: human neutrophil peptides HNP-1, HNP-2, and HNP-3. Defensin peptides have also been described in insects and higher plants. Dimarcq et al., "insect immunity: expression of the two major inducible antibacterial peptides, defensin and diptericin, in *Phormia terranvae,*" *EMBO J.*, vol. 9, pp. 2507–2515 (1990); Fisher et al., *Proc. Natl. Acad. Sci. USA*, vol. 84, pp. 3628–3632 (1987).

Slightly larger peptides called sarcotoxins have been purified from the fleshfly *Sarcophaga peregrina*. Okada et al., "Primary structure of sarcotoxin I, an antibacterial protein induced in the hemolymph of *Sarcophaga peregrina* (flesh fly) larvae," *J. Biol. Chem.*, vol. 260, pp. 7174–7177 (1985). Although highly divergent from the cecropins and defensins, the sarcotoxins presumably have a similar antibiotic function.

Other lytic peptides have been found in amphibians. Gibson and collaborators isolated two peptides from the African clawed frog, *Xenopus laevis*, peptides which they named PGS and Gly[10]Lys[22]PGS. Gibson et al., "Novel peptide fragments originating from $PGL_a$ and the caervlein and xenopsin precursors from *Xenopus laevis,*" *J. Biol. Chem.*, vol. 261, pp.5341–5349 (1986); and Givannini et al., "Biosynthesis and degradation of peptides derived from *Xenopus laevis* prohormones," *Biochem. J.*, vol.243, pp. 113–120 (1987). Zasloff showed that the Xenopus-derived peptides have antimicrobial activity, and renamed them magainins. Zasloff, "Magainins, a class of antimicrobial peptides from Xenopus skin: isolation, characterization of two active forms, and partial DNA sequence of a precursor," *Proc. Natl. Acad. Sci. USA*, vol. 84, pp. 3628–3632 (1987).

Synthesis of nonhomologous analogs of different classes of lytic peptides has been reported to reveal that a positively charged, amphipathic sequence containing at least 20 amino acids appeared to be a requirement for lytic activity in some classes of peptides. Shiba et al., "Structure-activity relationship of Lepidopteran, a self-defense peptide of *Bombyx more,*" *Tetrahedron*, vol.44, No. 3, pp. 787–803 (1988). Other work has shown that smaller peptides can also be lytic. See McLaughlin et al., cited below.

The synthetic lytic peptide known as S-1 (or Shiva 1) has been shown to destroy intracellular *Brucella abortus-*, *Trypanosoma cruzi-*, *Cryptosporidium parvum-*, and infectious bovine herpesvirus I (IBR)-infected host cells. See Jaynes et al., "In vitro effect of lytic peptides on normal and transformed mammalian cell lines," *Peptide Research*, vol. 2, No. 2, pp. 1–5 (1989); Wood et al., "Toxicity of a Novel Antimicrobial Agent to Cattle and Hamster cells In vitro," Proc. Ann. Amer. Soc. Anim. Sci., Utah State University, Logan, UT. *J. Anim. Sci.* (*Suppl.* 1), vol. 65, p. 380 (1987); Arrowood et al., "Hemolytic properties of lytic peptides active against the sporozoites of *Cryptosporidium parvum,*" *J. Protozool.*, vol. 38, No.6, pp. 161S-163S (1991); Arrowood et al., "In vitro activities of lytic peptides against the sporozoites of *Cryptosporidium parvum,*" *Antimicrob. Agents Chemother.*, vol. 35, pp. 224–227 (1991); and Reed et al., "Enhanced in vitro growth of murine fibroblast cells and preimplantation embryos cultured in medium supplemented with an amphipathic peptide," *Mol. Reprod. Devel.*, vol. 31, No. 2, pp. 106–113 (1992). Morvan et al., "In vitro activity of the antimicrobial peptide magainin 1 against *Bonamia ostreae*, the intrahemocytic parasite of the flat oyster *Ostrea edulis,*" *Mol. Mar. Biol.*, vol. 3, pp. 327–333 (1994) reports the in vitro use of a magainin to selectively reduce the viability of the parasite *Bonamia ostreae* at doses that did not affect cells of the flat oyster *Ostrea edulis*.

Also of interest are the designed peptides disclosed in McLaughlin et al., "Amphipathic Peptides," U.S. Pat. No. 5,789,542, issued Aug. 4, 1998; and Mark L. McLaughlin et al., "Short Amphipathic Peptides with Activity against Bacteria and Intracellular Pathogens," U.S. patent application Ser. No. 08/796,123, filed Feb. 6, 1997.

Lytic peptides such as are known generally in the art may be used in practicing the present inventions.

The complete disclosures of all references cited in this specification are hereby incorporated by reference. Also incorporated by reference is the full disclosure of the following document and unpublished manuscripts: Robert J. DeFatta, "The Eukaryotic Translation Initiation Factor (eIF) 4E During Cancer Progression and as a Target for Cancer Gene Therapy," a Dissertation, submitted to the Graduate Faculty of Medical Center of Louisiana State University and Agricultural and Mechanical College, catalogued and placed on the shelf on Mar. 20, 2001; R. J. DeFatta et al., "Selective Killing of Cancer Cells Based on Translational Control of a Suicide Gene," submitted to Nature Medicine, Jul. 9, 2001; and R. J. DeFatta et al., "A Cancer Gene Therapy Approach Through Translational Control of a Suicide Gene," submitted to Nature Medicine, Jul. 9, 2001. In the event of an otherwise irreconcilable conflict, however, the present specification shall control.

What is claimed is:

1. A DNA sequence comprising a promoter operatively linked to a transcription sequence; wherein the transcription sequence, when transcribed, produces a messenger RNA sequence that comprises a translatable sequence encoding a toxin, and an untranslated sequence; wherein the untranslated sequence inhibits translation of the toxin sequence under conditions that exist within normal mammalian cells that do not overexpress eukaryotic initiation factor eIF4E; wherein the untranslated sequence allows translation of the toxin sequence under conditions that exist within mammalian cells that everexpress eukaryotic initiation factor eIF4E relative to bormal cells; and wherein the untranslated sequence further comprises a hairpin secondary structure conformation having a stability measured as folded state free energy of $\Delta G \leq$ about $-50$ Kcal/Mol.

2. A DNA sequence as recited in claim 1, wherein the untranslated sequence allows translation of the toxin sequence under conditions which exist within mammalian cells that overexpress eukaryotic initiation factor eIF4E at least 2-fold greater relative to normal cells.

3. A DNA sequence as recited in claim 1, wherein the untranslated sequence comprises the 5' untranslated sequence selected from the group consisting of fibroblast growth factor-2, cyclin D1, proto-oncogene c-myc, vascular endothelial growth factor, and ornithine decarboxylase.

4. A DNA sequence as recited in claim 1, wherein the encoded toxin is a conditional toxin.

5. A DNA sequence as recited in claim 4, wherein the encoded conditional toxin is a herpes thymidine kinase.

6. A DNA sequence as recited in claim 5, wherein the untranslated sequence comprises the 5' untranslated sequence of fibroblast growth factor-2.

7. A DNA sequence as recited in claim 5, wherein the untranslated sequence comprises the 5' untranslated sequence selected from the group consisting of proto-oncogene c-myc, vascular endothelial growth factor, and ornithine decarboxylase.

8. A DNA sequence as recited in claim 1, wherein the untranslated sequence comprises a G/C-rich 5'UTR sequence.

9. A DNA sequence as recited in claim 8, wherein the untranslated wequence comprises mRNA with at least one substantially palindromic oligonucleotide sequence that is self-complimentary.

10. A DNA sequence as recited in claim 1, wherein the conditions that exist within mammalian cells that overexpress eukaryotic initiation factor eIF4E relative to normal cells are those that exist in metastatic tumor cells.

11. A messenger RNA sequence that comprises a translatable sequence encoding a toxin, and an untranslated sequence; wherein the untranslated sequence comprises an mRNA sequence with a secondary structure conformation having a stability measured as folded state free energy of $\Delta G \leq$ about $-50$ Kcat/Mol and wherein the untranslated sequence inhibits translation lf the toxin sequence under conditions that exist within normal mammalian cells that do not overexpress eukaryotic initiation factor eIF4E and wherein the untranslated sequence allows translation of the toxin sequence under conditions that exist within mammalian cells that overexpress eukaryotic initiation factor eIF4E relative to normal cells.

12. A vector comprising the DNA sequence of claim 1.

13. The vector of claim 12, wherein the vector is a viral vector.

14. The vector of claim 12, wherein the vector is a non-viral vector.

15. The vector of claim 13, wherein the vector is a BK vector.

16. A pharmaceutical composition comprising a therapeutically effective amount of the vector of claim 12 and a carrier.

17. The pharmaceutical composition of claim 16 wherein the carrier is a liposornal complex.

* * * * *

UNITED STATES PATENT AND TRADEMARK OFFICE
CERTIFICATE OF CORRECTION

PATENT NO. : 6,759,394 B2
DATED : July 6, 2004
INVENTOR(S) : Arrigo DeBenedetti and Robert J. DeFatta It is certified that error appears in the above-identified patent and that said Letters Patent is hereby corrected as shown below:

Column 22,
Line 41, please change "cells that everexpress eukaryotic" to -- cells that overexpress eukaryotic --.
Line 42, please change "...relative to bormal cells..." to -- ...relative to normal cells... --.

Column 23,
Line 5, please change "...untranslated wequence comprises..." to -- untranslated sequence comprises... --.
Line 17, please change "...about -50 Kcat/Mol..." to -- ...about -50 Kcal/Mol... --.
Line 18, please change "...inhibits translation if the toxin..." to -- ...inhibits translation of the toxin... --.

Column 24,
Line 17, please change "...is a liposomal complex..." to -- ...is a liposomal complex... --.

Signed and Sealed this

Twenty-third Day of November, 2004

JON W. DUDAS
*Director of the United States Patent and Trademark Office*